United States Patent [19]

Weddle

[11] Patent Number: Plant 6,492

[45] Date of Patent: Dec. 27, 1988

[54] ROSE PLANT

[76] Inventor: Von C. Weddle, 2801 Charlestown Rd., New Albany, Ind. 47150

[21] Appl. No.: 26,528

[22] Filed: Mar. 16, 1987

[51] Int. Cl.[4] ..... A01H 5/00

[52] U.S. Cl. ..... Plt./11

[58] Field of Search ..... Plt./11, 18–19

*Primary Examiner*—Robert E. Bagwill

*Attorney, Agent, or Firm*—Vincent G. Gioia

[57] ABSTRACT

A new light red, deep pink hybrid tea rose variety.

1 Drawing Sheet

The present invention relates to a new and distinct variety of rose plant of the hybrid tea rose class, which was originated by my crossing as seed parent the rose known as "First Prize" (U.S. Plant Pat. No. 2,774) and as pollen parent the rose known as "Swarthmore" (U.S. Plant Pat. No. 2,444). The denomination of this new rose is "Elizabeth Taylor".

Among the novel characteristics possessed by this new variety which distinguish it from its parents and all other varieties of which I am aware are its large light red, deep pink flowers of good exhibition form which are attractively displayed against shiny dark green foliage and which are long lasting on the plant and after cutting. Asexual reproduction by budding of the new variety as performed in Floyd County, Ind., shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (R.H.S.C.C.). The Terminology used in color description herein refers to plate numbers in the aforementioned color chart, e.g., "60D" is plate 60D of The Royal Horticultural Society Colour Chart.

Parentage: Seedling.

*Seed parent.*—"First Prize".

*Pollen parent.*—"Swarthmore".

Class: Hybrid Tea.

The following observations are made of specimens grown outdoors in Floyd County, Ind., during the month of July.

FLOWER

Blooming habit: Continuous.

A. Bud:

(1) *Size.*—Medium.

(2) *Form.*—Long pointed.

(3) *Color.*—As sepals divide, buds are near 60D.

(4) *Sepals.*—Long, simple.

(5) *Peduncle.*—Length — average. Aspect — straight. Strength — erect. Color — medium green.

B. Bloom:

(1) *Size.*—Average size when fully expanded — about 4½ to 5 inches.

(2) *Borne.*—Singly, one to a stem.

(3) *Form.*—High centered, blooms of good exhibition form. Outer petals roll under. Flowers open well.

(4) *Petalage.*—Number of petals under normal conditions — about 30 to 33.

(5) *Color.*—After sepals fall and petals unfurl, flower coloring is predominantly light red, deep pink near 73A to 73B. However, in one-half open blooms outer petals are near 60D. Flowers generally lighten in tonality upon aging.

C. Petals:

(1) *Texture.*—Thick, good substance.

(2) *Appearance.*—Inside velvety and outside satiny.

(3) *Form.*—Broad, fan shaped.

(4) *Arrangement.*—Regularly arranged.

(5) *Petaloids in center.*—Few.

(6) *Persistance.*—Persist.

(7) *Fragrance.*—Slight.

(8) *Lasting quality.*—Very long lasting quality on plant and as cut flower.

REPRODUCTIVE ORGANS

A. Stamens, filaments and anthers:

*Arrangement and color.*—Regularly arranged. Color — yellow.

B. Pollen:

*Color.*—Yellow.

C. Styles: Even, medium length.

D. Stigmas:

*Color.*—Pinkish yellow.

E. Hips: Globular, average size, light yellow when mature, seeds protrude intermittently.

PLANT

A. Form: Upright, slightly spreading.

B. Growth: Very vigorous.

*Height attained.*—About 5 to 6 feet.

C. Foliage: Compound 5 to 7 leaflets.

(1) *Size.*—Large.

(2) *Quantity.*—Abundant.

(3) *Color.*—New foliage: Upper side — reddish green. Under side — same. Old foliage: Upper side — dark green. Under side — green.

(4) *Shape.*—Oval, acuminate.

(5) *Texture.*—Upper side is leathery, glossy; under side is glaborous.

(6) *Edge.*—Serrate.

(7) *Serration.*—Ordinary.

(8) *Leaf stem.*—Color — reddish green. Under side — same.

(9) *Stipules.*—Medium, slightly bearded.

(10) *Resistance to disease.*—Blackspot — average. Mildew — average. Rust — average.

D. Wood:

(1) *New wood.*—Color — reddish green. Bark — smooth.

(2) *Old wood.*—Color — medium green. Bark — smooth.

E. Thorns:

(1) *Thorns.*—Quantity (main stalk) — average. On laterals from stalk — average. Form — ordinary, thin, pointed. Length — medium. Color — light pink. Position — regular.

(2) *Prickles.*—Yes.

F. Winter hardiness: Needs protection in severe climate.

I claim:

1. A new and distinct variety of rose plant of the hybrid tea rose class, substantially as shown and described, characterized particularly by large light red, deep pink colored flowers of good exhibition form attractively displayed against shiny dark green foliage and which are long lasting on the plant and as cut flowers.

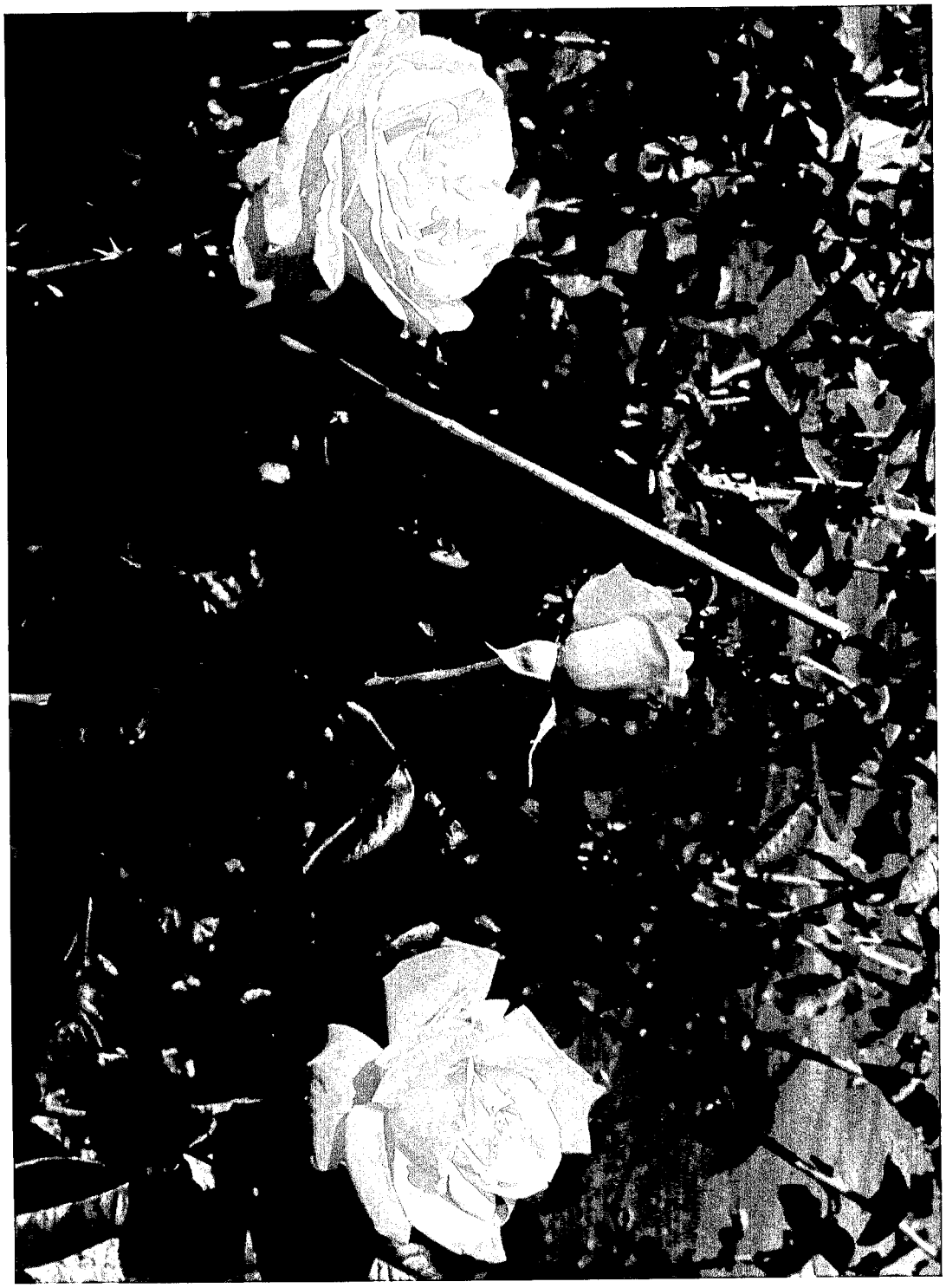

* * * * *